United States Patent [19]
Day et al.

[11] Patent Number: 4,987,266
[45] Date of Patent: Jan. 22, 1991

[54] PROCESS FOR THE MANUFACTURE OF NITROPHENETOLE

[75] Inventors: Richard J. Day, Creve Coeur; Harry B. Harlow, Fenton; Dennis C. Owsley, St. Louis, all of Mo.

[73] Assignee: Monsanto Company, St. Louis, Mo.

[21] Appl. No.: 459,016

[22] Filed: Dec. 29, 1989

[51] Int. Cl.$^5$ .................. C07C 79/35; C07C 41/16
[52] U.S. Cl. .................................. 568/584; 568/939
[58] Field of Search ........................... 568/584, 939

[56] References Cited

U.S. PATENT DOCUMENTS

| | | | |
|---|---|---|---|
| 3,085,113 | 4/1963 | Knowles et al. | 568/584 |
| 3,634,518 | 1/1972 | Bentz et al. | 568/2 |
| 4,287,125 | 9/1981 | Soula | 549/451 |
| 4,377,712 | 3/1984 | Foster et al. | 568/635 |
| 4,454,355 | 6/1984 | Schubert et al. | 568/584 |
| 4,469,893 | 9/1984 | Tang et al. | 568/424 |
| 4,479,015 | 10/1984 | Sasson et al. | 568/584 |
| 4,740,330 | 4/1988 | Wana et al. | 552/115 |
| 4,782,190 | 11/1988 | Kasbauer et al. | 568/584 |

FOREIGN PATENT DOCUMENTS 2639700 3/1976 Fed. Rep. of Germany .
62677 3/1970 Romania .

Primary Examiner—Robert L. Stoll
Assistant Examiner—Chhaya Sayala
Attorney, Agent, or Firm—Stanley M. Tarter; Wayne R. Eberhardt

[57] ABSTRACT

A process is provided for producing nitrophenetole where nitrochlorobenzene is reacted in a cosolvent of a monohydric alcohol and N-alkylpyrrolidone with aqueous alkali metal hydroxide.

15 Claims, No Drawings

PROCESS FOR THE MANUFACTURE OF NITROPHENETOLE

BACKGROUND OF THE INVENTION

1. Field of the Invention

The present invention relates to a new and improved process for the manufacture of nitrophenetole. More particularly, the present invention relates to the manufacture of nitrophenetole by the ethoxylation of p-nitrochlorobenzene wherein the reaction is carried out in the presence of oxygen to suppress the formation of azo and azoxy compounds as by-products and wherein nitrophenetole is produced with greater conversions and greater yields.

2. Prior Art

For a variety of organic syntheses p-nitrophenetole is an important chemical intermediate. One significant commercial use of p-nitrophenetole is as an intermediate chemical in the manufacture of p-phenetidine. p-Phenetidine is an important intermediate in the manufacture of ethoxyquin, the common name of 2,2,4-trimethyl-6-ethoxy-1-H-dihydroquinoline. Ethoxyquin has found wide commercial use in reducing or suppressing the oxidation of oils in animal feeds and the like. Animal feeds having an effective antioxidant amount of ethoxyquin have significantly longer shelf life than feeds not having the same incorporated therein. p-Phenetidine is also an important intermediate compound useful in the manufacture of phenacetin, phenocoll, p-phenetyl-urea and various dyestuff intermediates.

A well-known method for the manufacture of p-nitrophenetole involves the ethoxylation of p-nitrochlorobenzene in an ethanolic solution containing an alkali metal hydroxide, such as sodium hydroxide according to the following equation:

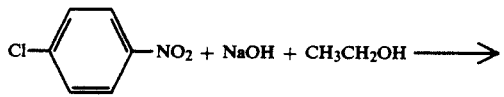

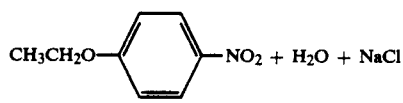

Unfortunately, this known reaction is plagued with the formation of azo and azoxy compounds as undesirable by-products. These by-products are the result of an exothermic side reaction of p-nitrochlorobenzene under the reaction conditions normally employed. The by-products have been identified as 4,4-dichloroazoxybenzene and 4,4'-dichloroazobenzene. When p-nitrochlorobenzene is reacted with ethanol in the presence of an aqueous solution of alkali metal hydroxide, the azo and azoxy by-products may be produced in yields as high as 40 mol percent and higher. Accordingly, in commercial production of p-nitrophenetole steps are taken to minimize or suppress the runaway exothermic reactions that result in the formation of the azo and azoxy by-products. One effective way to control the formation of the azo and azoxy by-products is to introduce molecular oxygen in the liquid reaction mixture of p-nitrochlorobenzene, ethanol and aqueous sodium hydroxide. In order to optimize the control of the formation of the by-products, the oxygen content in the headspace above the reaction mixture is usually maintained above 15 mol percent. Oxygen being present in such high amount, together with ethanol, gives rise to a potential flammability and explosion hazard. As will be appreciated, a desired end would be to carry out the reaction at a lower oxygen content in the headspace while controlling the formation of azo and azoxy by-products. The present invention discloses a method that enables one to carry out the reaction of p-nitrochlorobenzene and ethanol with alkali metal hydroxide at significantly reduced levels of headspace oxygen while at the same time minimizing the formation of the azo and azoxy compounds.

U.S. Pat. No. 3,085,113 describes the ethoxylation of p-nitrochlorobenzene to produce p-nitrophenetole in the presence of air to suppress the occurrence of side reactions that result in the production of undesirable azo and azoxy compounds. In accordance with this known process, the air quantity must be carefully controlled in order to suppress the side reactions forming the azo and azoxy compounds.

Romanian Patent No. 62,677 discloses a process wherein the ethylation of p-nitrophenol with ethyl chloride is carried out in a polar aprotic solvent. In this known process, p-nitrophenol is used in the form of anhydrous sodium salts with the introduction of gaseous ethyl chloride as it is consumed in the reaction. N,N-dimethylformamide, N,N-dimethylacetamide and N-methylpyrrolidone are mentioned in the patent as suitable polar aprotic solvents.

German Patent No. 2,639,700 describes the synthesis of p-nitrophenetole by reacting p-nitrochlorobenzene with ethanol in the presence of an alkali metal hydroxide in dimethyl sulfoxide solvent. This known method is not concerned with the use of an air sparge to minimize the formation of the azo and azoxy by-products.

U.S. Pat. No. 4,782,190 discloses preparing p-nitrophenetole by reaction of p-nitrochlorobenzene with ethanol and alkali metal hydroxides in the presence of a phase-transfer catalyst, such as the customary quaternary organic ammonium salts.

SUMMARY OF THE INVENTION

The present invention provides an improved process for producing p-nitrophenetole wherein p-nitrochlorobenzene is reacted at an elevated temperature with ethanol in the presence of an aqueous solution of an alkali metal hydroxide and wherein the reaction mixture is sparged with an oxygen-containing gas to suppress the formation of azo and azoxy compounds. In accordance with the present invention, one is able to carry out the reaction at reduced levels of oxygen while continuing to suppress the formation of the azo and azoxy by-products. At the reduced levels of oxygen, the potential flammability and explosion hazard of the ethanol vapors in the headspace of the reactor is significantly reduced. Also, in the process of the present invention optimal yields of p-nitrophenetole can be obtained using a concentration of only about 50% alkali metal hydroxide solution instead of a much higher concentration of alkali metal hydroxide. Using lower concentrations of alkali metal hydroxide in water is advantageous as compared to the use of higher concentrations of alkali metal hydroxide in water since at room temperature a highly concentrated solution of alkali metal hydroxide may be a solid rather than a liquid which is easier to handle. The improvement of the present invention is obtained by incorporating in the reaction mixture of nitrochlorobenzene, a monohydric alcohol, an alkali metal hydroxide solution, and, as a cosolvent, N-alkyl-pyrrolidone, preferably N-methylpyrrolidone. The alkyl substitutent may have one to about 8 carbon atoms.

In the process of the present invention p-nitrochlorobenzene and a lower monohydric alcohol, such as ethanol, are brought into reactive contact in a closed reaction vessel with excess aqueous alkali metal hydroxide, preferably sodium hydroxide solution, and heated while the resulting mixture is being sparged with a gas containing less than 12% oxygen, preferably less than 10% oxygen with the remainder being an inert gas, such as nitrogen. In the reaction mixture the N-alkylpyrrolidone is present as a cosolvent with the ethanol. After completion of the ethoxylation, the resulting p-nitrophenetole is separated from the reaction mixture.

While the present invention has been described primarily as a process for producing nitrophenetole, it is understood that the process of the invention is also useful in preparing p-nitroanisole and o-nitroanisole. To prepare p-nitroanisole one would react p-nitrochlorobenzene with methanol. To prepare o-nitroanisole one would react o-nitrochlorobenzene with methanol. o-Nitrophenetole can be prepared from o-nitrochlorobenzene and ethanol.

DETAILED DESCRIPTION OF THE INVENTION

In accordance with the present invention nitrochlorobenzene, sodium hydroxide and ethanol are reacted to produce nitrophenetole. The nitrochlorobenzene will normally be at least 99% p-nitrochlorobenzene with the remainder being o-nitrochlorobenzene and m-nitrochlorobenzene. The p-nitrochlorobenzene is dissolved in ethanol and N-methylpyrrolidone. For good results, the ethanol is employed in stoichiometric excess. A mol ratio of 5:1 to 1:1 of ethanol to p-nitrochlorobenzene is usually employed but preferably a mol ratio of about 4:1 to 1:1 of ethanol to p-nitrochlorobenzene is employed. The ethanol can be used both in the pure form and as an industrial product of 95% ethanol and 5% water. A mol ratio of N-methylpyrrolidone to p-nitrochlorobenzene is about 4:1 to 1:1. Preferably the mol ratio of N-methylpyrrolidone is 2.5:1. The solution containing ethanol, p-nitrochlorobenzene and N-methylpyrrolidone is heated, preferably to about 60°-80° C., more preferably to about 70°-75° C. To this heated solution, aqueous sodium hydroxide is slowly added, preferably with stirring over an extended period of time at rate of 0.2 to 1.0 mol of caustic per mol of p-nitrochlorobenzene per hour. The caustic solution contains about 40-60 weight percent sodium hydroxide. For best results the concentration of hydroxide is between about 45-55%. Initially, the reactor is provided with an inert gas blanket. During the reaction, the reaction mixture is sparged with a gas containing less than about 12% oxygen, preferably less than about 10% oxygen. The reaction is carried out from about 1 to 5 atmospheres of pressure. Such a gas may be an air-nitrogen mixture wherein the two gases are pre-mixed so that the oxygen content is at the desired reduced level. Sparging of the gas mixture is continued during the reaction at a rate sufficient to provide an oxygen headspace content of less than 5%, preferably about 1-3%. The p-nitrochlorobenzene will be converted to about 96% by weight p-nitrophenetole and about 4% by weight p-nitrophenol, along with minimum amounts of azo and azoxy by-products as well as the ortho isomers of nitrophenetole and nitrophenol.

The p-nitrophenetole product is separated from the resulting reaction mixture. This may be accomplished by cooling the reaction mixture to about 50°-70° C. and maintaining this reduced temperature while adding a strong mineral acid, preferably hydrochloric acid, to neutralize excess caustic. With this neutralization, remaining alkali metal ions precipitate as the chloride and are removed by filtration. The filtration can be carried out either before or after removal of the ethanol and water by distillation from the reaction mixture. After the ethanol and water are removed, N-methylpyrrolidone is removed, preferably under vacuum, in a separate distillation operation.

p-Nitrophenol is separated from p-nitrophenetole by the use of aqueous caustic wash. This is accomplished by contacting the material from which water, ethanol and N-methylpyrrolidone have been distilled, with dilute caustic solution, preferably 3 to 5% aqueous sodium hydroxide. p-Nitrophenol will dissolve in the alkaline solution but p-nitrophenetole will not. Thus, a two-phase system results with the p-nitrophenol being dissolved in the aqueous phase and with p-nitrophenetole comprising the nonaqueous phase. The temperature during caustic wash and phase separation is maintained at a level sufficiently high so that the p-nitrophenetole is a liquid. Finally, the liquid p-nitrophenetole is cooled to room temperature to produce solid p-nitrophenetole.

The following examples will serve to more particularly illustrate the present invention without being deemed to be limitative thereof. Where parts are used, they are to be interpreted as parts by weight unless otherwise indicated.

EXAMPLE 1

The reactor is charged with 97.45 parts of fresh p-nitrochlorobenzene, 98.61 parts of fresh and recycled ethanol, 0.05 parts of fresh N-methylpyrrolidone (NMP) and 163.59 parts of recycled NMP containing 10.98 parts of recycled p-nitrophenetole, 5.92 parts of recycled p-nitrochlorobenzene and 3.56 parts of recycled water. In addition to these materials, the fresh p-nitrochlorobenzene contains 0.78 parts of o-nitrochlorobenzene and the recycled NMP contains 0.03 parts of o-nitrochlorobenzene and 0.09 parts of recycled o-nitrophenetole. The recovered ethanol also contains small amounts of p-nitrochlorobenzene and o-nitrochlorobenzene. The reactor is sparged with a gas mixture containing 12% oxygen in nitrogen at ca. 900 mL/hr-g-mol of p-nitrochlorobenzene and heated to 74° C. under a nitrogen blanket. A total of 78.77 parts of 50% sodium hydroxide in water is added to the reactor through a dip tube over 3.42 hr. At the end of the reaction period, the reactor is held at 74° C. for an additional 4.58 hr, making a total reaction time of 8 hr. The reaction mixture is then cooled to 60° C. and neutralized with 47 parts of 28% HCl. The HCl needed for the neutralization is calculated from a final titration to determine caustic concentration remaining in the reactor. The reaction mass is sent to a still pot to recover ethanol. Two recycle streams are added to the still pot. These streams are recovered ethanol from a subsequent salt wash(71.76 parts) and recycle water from the isolation of solid p-nitrophenol and dehydration of p-nitrophenetole (48.46 parts). The stream now contains 116.26 parts of p-nitrophenetole, 6.82 parts of p-nitrochlorobenzene, 4.16 parts of p-nitrophenol, 148.55 parts of NMP, 59.52 parts of sodium chloride, 19.48 parts of ethanol, 153.56 parts of water and 0.99 parts of other organics (o-nitrochlorobenzene, o-nitrophenetole, o-nitrophenol).

Ethanol is recovered as a 92% ethanol stream 130.2 parts) overhead at a still pot temperature of 116° C. The distillation is run at atmospheric pressure.

The still pot now contains 116.24 parts of p-nitrophenetole, 6.80 parts of p-nitrochlorobenzene, 4.16 parts of p-nitrophenol, 148.55 parts of NMP, 59.52 parts of sodium chloride, 0.30 parts of ethanol, 142.58 parts of water and 0.99 parts of other organics (o-nitrophenol, o-nitrochlorobenzene and o-nitrophenetole). The distilled bottoms are transferred to the water stripping still.

The water stripping column is run at 100° C. at the condenser and 194° C. in the still pot. Water (139.38 parts) is taken off overhead. The water overhead contains 0.30 parts of ethanol, 0.04 parts of NMP and 0.03 parts of o-nitrophenol. The overheads are discarded.

The residue in the still pot is sent to a filter to recover sodium chloride. The sodium chloride remaining on the filter is washed with 59.52 parts of 95% ethanol. The ethanol wash is recycled to the ethanol recovery still pot and contains p-nitrophenetole (6.59 parts), p-nitrochlorobenzene (0.31 parts), NMP (5.49 parts), p-nitrophenol (0.18 parts), ethanol (55.95 parts), sodium chloride (0.21 parts), o-nitrophenetole (0.05 parts) and water (2.98 parts).

The salt (59.30 parts, containing small amounts of p-nitrophenetole, p-nitrochlorobenzene, p-nitrophenol, NMP, ethanol, o-nitrophenetole and o-nitrochlorobenzene) is discarded.

The mother liquor from the salt filtering operation (267.61 parts) is sent to the solvent stripping stillpot. The solvent stripping still column is run at a pressure of 50 mm Hg at the condenser at a temperature 81° C. The temperature and pressure in the still pot is 192° C. and 57 mm Hg, respectively. The overheads from this stripping still (163.59 parts) are returned to the reactor. These overheads contain 10.98 parts of p-nitrophenetole, 5.92 parts of p-nitrochlorobenzene, 143 parts of NMP, 3.56 parts of water, 0.03 parts of o-nitrochlorobenzene and 0.09 parts of o-nitrophenetole.

The residue in the solvent stripping still pot is cooled to 65° C. and added to an extractor. This residue contains 98.67 parts of p-nitrophenetole, 0.57 parts p-nitrochlorobenzene, 3.98 parts of p-nitrophenol, 0.02 parts of o-nitrochlorobenzene, 0.77 parts of o-nitrophenetole and 0.01 parts of NMP. The extractor is operated at 65° C. so that the p-nitrophenetole remains a liquid. A ca. 4% solution of sodium hydroxide (31.19 parts) is added and the layers are separated. Then the organic layer is washed with 12 parts of clean water.

The water washes are combined and contain the sodium salt of p-nitrophenol at a concentration of ca. 10%. The organic layer from the extractor (101.97 parts) is taken to the p-nitrophenetole dehydration still pot. Treatment of the water layer from the caustic/water washing operations is described below. The dehydration still is run at a pot temperature of 150° C. and 350 mm Hgpressure. The overhead stream from the dehydrator (1.97 parts) is combined with the recycle water from the p-nitrophenol recovery section of the process as described below. The product in the dehydrator still pot (100.0 parts) contains 98.64 parts of p-nitrophenetole, 0.57 parts of p-nitrochlorobenzene, and 0.77 parts of o-nitrophenetole.

The combined caustic and water washes from the extractor are acidified to a pH of 5.5–6.0 with 28% HCl (3.91 parts). The solution is cooled to 30°–35° C. to precipitate solid p-nitrophenol. The solid is (3.97 parts) is isolated on a small filter. The mother liquor from this operation is mixed with the dehydrator overhead and returned to the ethanol recovery still pot (48.46 parts).

EXAMPLE 2

The procedure of Example 1 was generally followed, except that the reaction was run at 85° C., 73% sodium hydroxide was used to feed the stirred reactor and air was used as the sparging gas and no N-methylpyrrolidone was used as a cosolvent. The reactor headspace contained more that 15 mol % oxygen.

In Example 1, the reactor headspace contained less than 3 mol % oxygen. In Example 1, the conversion of p-nitrochlorobenzene is 94.7% in eight hours, whereas in Example 2 the conversion of p-nitrochlorobenzene is only 70% in eight hours. In Example 1, the yield of p-nitrophenetole was 95.3%, whereas in Example 2 the yield of p-nitrophenetole is 93.5%. Also, for every 100 parts of p-nitrophenetole produced in accordance with Example 1, 3.5 parts of p-nitrophenol by-product was produced. On the other hand, for every 100 parts of p-nitrophenetole produced in Example 2, 4.0 parts of p-nitrophenol by-product is produced.

As can be seen, improved conversions and yields of p-nitrochlorobenzene at lower temperatures are obtained in practicing the present invention. Improved yields of p-nitrophenetole and a reduction in the production of by-product p-nitrophenol are also obtained in practicing the present invention. This represents a significant improvement in the art. Also, the practice of the present invention is advantageous in that a sparging gas containing a lesser amount of oxygen (below about 12%) can be used to satisfactorily suppress the production of the oazoxybenzene and 4,4'- (dichloroazobenzene by-products. At the lower levels of oxygen employed in the present invention, there is less likelihood of producing potentially explosive mixtures of ethanol and oxygen.

What is claimed is:

1. In a process for producing p-nitrophenetole where nitrochlorobenzene is reacted in a monohydric alcohol solution with aqueous alkali metal hydroxide using an oxygen-containing gas sparge to suppress the production of azo and azoxy by-products, the improvement of carrying out the reaction in the presence of an effective amount of an N-alkylpyrrolidone wherein the alkyl substituent has 1 to 8 carbon atoms.

2. The process of claim 1 wherein the pyrrolidone additive is N-methylpyrrolidone.

3. The process of claim 1, wherein the alkali metal hydroxide is sodium hydroxide.

4. The process of claim 1, wherein the alkali metal hydroxide is potassium hydroxide.

5. The process of claim 1, wherein the monohydric alcohol is ethanol.

6. A process of preparing p-nitrophenetole comprising the steps of
 (a.) bringing p-nitrochlorobenzene, ethanol and sodium hydroxide into reactive contact in a cosolvent system comprising ethanol, water and N-methylpyrrolidone.
 (b.) sparging the reaction mixture of step (a) with an oxygen-containing gas wherein the oxygen content is less than about 12% by volume of the gas; and (c.) separating the thus-produced p-nitrophenetole from the resulting reaction product.

7. The process of claim 6 wherein the reaction is carried out at an elevated temperature.

8. The process of claim 6 wherein the reaction temperature is about 60°-80° C.

9. The process of claim 6 wherein the reaction temperature is about 70°-75° C.

10. A process of preparing p-nitrophenetole comprising the steps of:
(a.) bringing p-nitrochlorobenzene, ethanol and 40–40–60% aqueous solution of sodium hydroxide into reactive contact at an elevated temperature in a cosolvent liquid system comprising the solvents of ethanol, water and N-methylpyrrolidone to ethoxylate the p-nitrochlorobenzene to produce p-nitrophenetole, the mol ratio of ethanol to p-nitrochlorobenzene being about 5:1 to 1:1 and the mol ratio of N-methylpyrrolidone to p-nitrochlorobenzene being about 4:1 to 1:1;
(b) sparging the reaction mixture with an oxygen containing gas wherein the oxygen content is less than about 12% by volume of the gas to suppress the production of azo and azoxy by-products; and
(c) separating the produced p-nitrophenetole from the resulting reaction product.

11. A process of preparing p-nitrophenetole by ethoxylation of p-nitrochlorobenzene comprising the steps of:
(a) charging a reactor with p-nitrochlorobenzene, ethanol and N-methylpyrrolidone.
(b) adding 40–60% aqueous sodium hydroxide solution dropwise to the mixture of step (a) while sparging the reaction mixture with an oxygen-containing gas wherein the oxygen content is less than about 12% by volume of the gas to suppress the production of azo and azoxy by-products; and
(c) separating the produced p-nitrophenetole from the resulting reaction product.

12. A process of preparing p-nitrophenetole by ethoxylation of p-nitrochlorobenzene comprising the steps of:
(a) charging a reactor with p-nitrochlorobenzene, ethanol and N-methlypyrrolidone;
(b) adding 40–60% aqueous sodium hydroxide solution dropwise to the mixture of step (a) while sparging the reaction mixture with an oxygen-containing gas, wherein the oxygen content is less than about 10% by volume of the gas, the mol ratio of ethanol to p-nitrochlorobenzene being about 4:1 to 1:1 and the mol ratio of N-methylpyrrolidone to p-nitrochlorobenzene being about 2.5:1 to 1:1; and
(c) separating the produced p-nitrophenetole from the resulting reaction produced.

13. The process of claim 12 wherein its reaction temperature is about 60°-80° C.

14. The process of claim 13 wherein the reaction temperature is about 70°-75° C.

15. A process of preparing p-nitrophenetole by ethoxylation of p-nitrochlorobenzene comprising the steps of:
(a) charging a reaction vessel with p-nitrochlorobenzene, ethanol and N-methylpyrrolidone, the mol ratio of ethanol to p-nitrochlorobenzene being about 5:1 to 1:1 and the mol ratio of N-methylpyrrolidone to p-nitrochlorobenzene being about 4:1 to 1:1;
(b) heating the contents of the reactor to a temperature of about 60°-80° C.;
(c) adding 40–60% aqueous sodium hydroxide dropwise to the mixture of step (a) while sparging the reaction mixture with an oxygen-containing gas to suppress the formation of azo and azoxy by-products wherein the oxygen content is less than about 12% by volume of the gas while maintaining a headspace oxygen content of the reactor at about 1–5%, whereby p-nitrophenetole and a minor amount of p-nitrophenol are produced;
(d) neutralizing the resulting reaction mixture with hydrochloric acid solution;
(e) removing unreacted ethanol from the reaction mixture by distillation;
(f) removing water from the reaction mixture by distillation, whereby sodium chloride is precipitated;
(g) removing the precipitated sodium chloride from the reaction mixture by filtration;
(h) removing n-methylpyrrolidone from the reaction mixture by distillation;
(i) contacting the residue of step (h) with a dilute solution of sodium hydroxide to form an aqueous phase containing the p-nitrophenol and an organic layer of p-nitrophenetole; and
(j) dehydrating the organic layer of step (i) to produce p-nitrophenetole in solid form.

* * * * *